United States Patent

Quinn

Patent Number: 5,498,249
Date of Patent: Mar. 12, 1996

[54] CATHETER STYLET

[75] Inventor: Kathryn A. Quinn, Grayslake, Ill.

[73] Assignee: Radius International, Inc., Grayslake, Ill.

[21] Appl. No.: 217,447

[22] Filed: Mar. 24, 1994

[51] Int. Cl.⁶ ................................. A61M 25/00
[52] U.S. Cl. .................... 604/280; 604/170; 604/282; 128/772
[58] Field of Search .................. 604/280, 264, 604/266, 267, 164, 170, 281, 282; 128/656–658, 772

[56] References Cited

U.S. PATENT DOCUMENTS

| | | | |
|---|---|---|---|
| 1,767,073 | 6/1930 | Ingold | 604/266 |
| 3,709,211 | 1/1973 | Hawkins | 604/267 |
| 4,496,347 | 1/1985 | MacLean et al. | 128/657 |
| 4,559,046 | 12/1985 | Groshong et al. | 128/658 |
| 4,798,593 | 1/1989 | Iwatschenko | 604/170 |
| 4,824,435 | 4/1989 | Giesy et al. | 128/772 |
| 5,108,368 | 4/1992 | Hammerslag et al. | 604/280 |
| 5,231,989 | 8/1993 | Middleman et al. | 128/657 |
| 5,284,474 | 2/1994 | Adair | 604/164 |
| 5,303,714 | 4/1994 | Abele et al. | 128/772 |

FOREIGN PATENT DOCUMENTS 9311823  6/1993  WIPO ................... 604/264

*Primary Examiner*—C. Fred Rosenbaum
*Assistant Examiner*—Ronald K. Stright, Jr.

[57] ABSTRACT

The present invention is directed to a catheter tube assembly for the internal administration or aspiration of fluids to the body cavity of a patient. The assembly includes a catheter tube and a stylet. The catheter tube has a passage section with the stylet being disposed in the passage section. The stylet has an elongate body portion having distal and proximal ends. The stylet also includes a terminal end. A first leg and a second leg interconnect the body portion to the terminal end. The stylet further includes a support portion located between the body portion and the terminal end. In one aspect of the invention, the support portion and the terminal end from a circular loop.

15 Claims, 1 Drawing Sheet

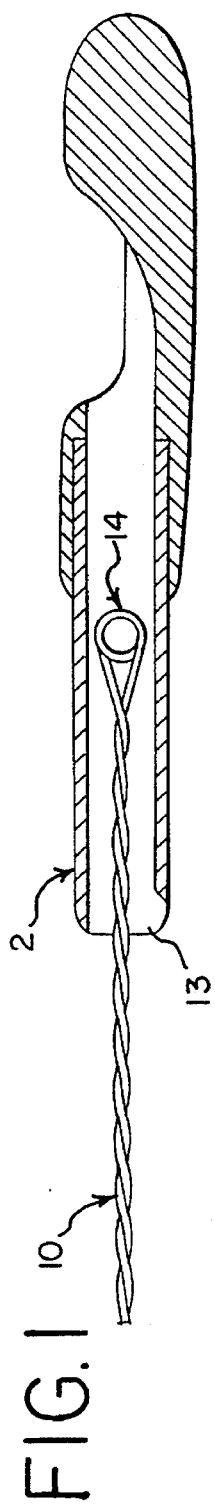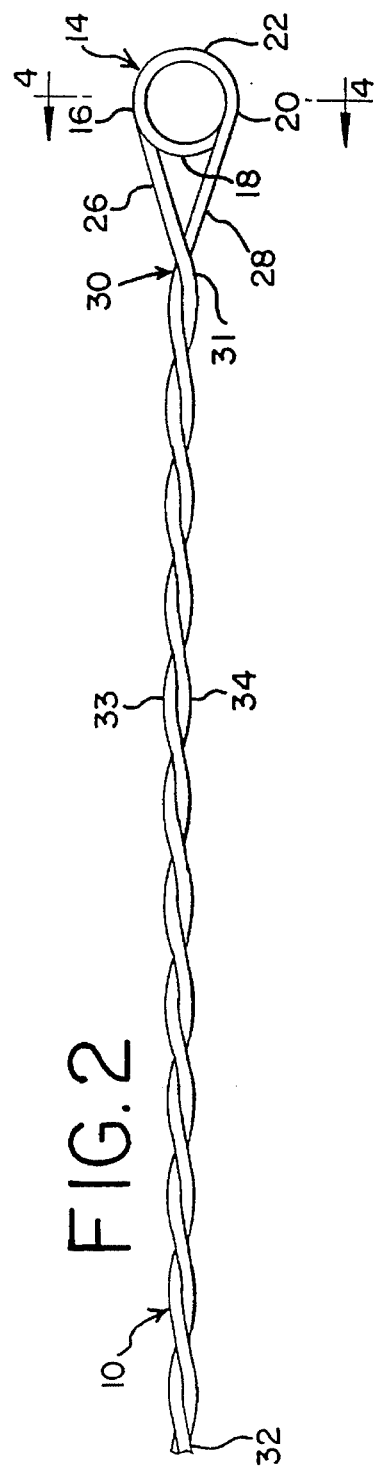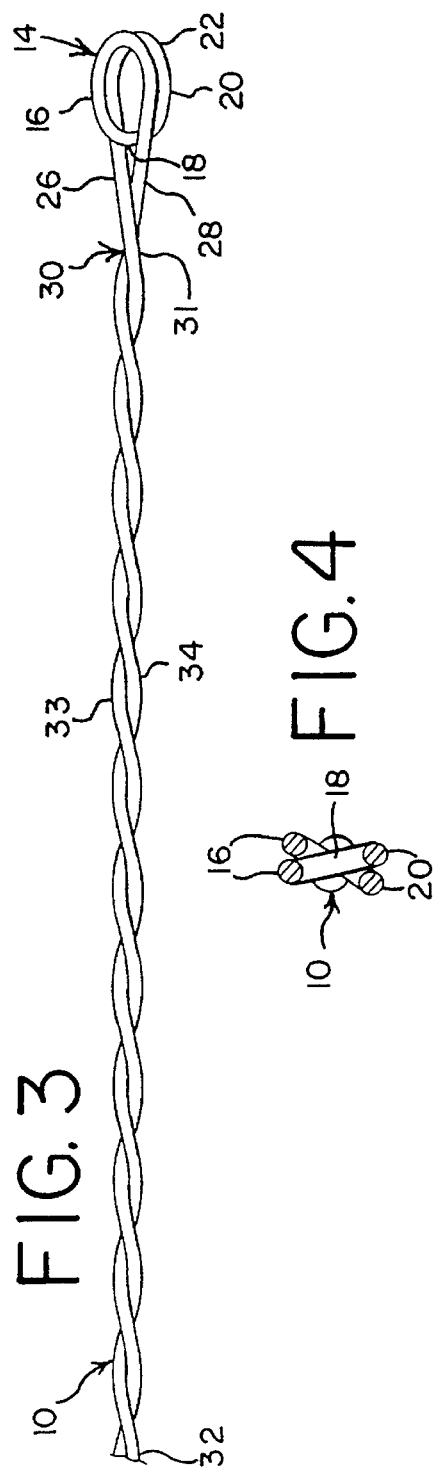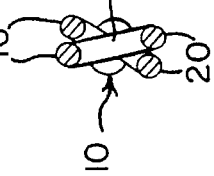

CATHETER STYLET

BACKGROUND OF THE INVENTION

The present invention relates generally to the intubation of patients for the internal administration or aspiration of fluids to a patient. More particularly, the present invention relates to a catheter tube and stylet assembly and an improved stylet for use with a catheter.

During various medical procedures, catheters are used for enteral feeding, urinary bladder drainage and irrigation, suctioning of blood and mucous, as well as for other purposes in the medical treatment of humans. The catheter is a flexible tube that must be placed through an orifice of the patient and advanced into the desired location. For example, during enteric therapy, a catheter or feeding tube is inserted through the nose of a patient and is carefully advanced into the patient's stomach or intestinal tract. Once properly positioned, fluids may be passed through the feeding tube and into the body of the patient. Often, these feeding tubes include a bolus having one or more apertures located therein in order to allow the fluids to pass from the feeding tube into the patient.

Since the catheter tube is relatively flexible, the rigidity of the catheter must be increased during the intubation process in order to allow for the insertion of the feeding tube into the patient. One approach is to increase the rigidity of the feeding tube through the use of a semi-rigid stylet removably mounted within the feeding tube. This approach allows the medical personnel to increase the rigidity of the feeding tube during the intubation process and thus assists in the proper placement of the feeding tube. Once the feeding tube is properly positioned within the patient, the stylet is removed from the feeding tube so that the feeding tube will become flexible again.

Two exemplary stylets are shown in U.S. Pat. No. 4,496,347 issued to MacLean et al. First, FIGS. 3 and 8–9 show a stylet formed from an elongate wire having a ball-shaped bead at its distal or insertion end. This stylet is disfavored because the bead may exit the feeding tube from the apertures within the bolus. Accordingly, the bead could strike a patient's tissues thereby causing injury. In addition, this stylet is more complex to manufacture than other known stylets because the ball-shaped bead must be separately attached to the wire.

A second known stylet is shown in FIGS. 5–7 of the '347 patent. This stylet is formed from a single strand of wire that is bent in half and twisted around itself in a double helix type formation. At the distal end of the stylet an elongated loop is formed from a single strand of wire. Generally, the loop has a length greater than the diameter of the apertures of the associated feeding tube in order to prevent the escape of the stylet from within the feeding tube. However, the loop may be easily deformed because it is formed from a single strand of wire. In particular, the side arms of the loop have no support and may be easily bent or distorted upon the application of pressure. As a result, the deformed loop may then exit the bolus and strike the tissues of a patient.

Accordingly, a need remains for a stylet that is easily manufactured and cannot be deformed so as to escape from within the associated catheter tube.

SUMMARY OF THE INVENTION

A primary object of the present invention is to provide an improved stylet for use with a catheter tube.

Another object is to provide a stylet that is nondeformable so as not to escape from the associated catheter tube.

An additional object is to provide a stylet that is safer for patient use than other known stylets.

A further object is to provide a stylet that is less expensively and more easily manufactured than stylets presently in use.

Yet another object is to provide an improved catheter tube assembly including a catheter tube and a stylet.

The foregoing and other objects are realized in accord with the present invention by providing a catheter tube assembly for the internal administration or aspiration of fluids to the body cavity of a patient. The assembly includes a catheter tube and a stylet. The catheter tube has a passage section with the styler being disposed in the passage section. The stylet has an elongate body portion having distal and proximal ends. The stylet also includes a terminal or insertion end. A first leg and a second leg interconnect the distal end of the body portion to the terminal or insertion end, of the stylet. The stylet further includes a support portion located between the distal end of the body portion and the terminal or insertion end.

In one aspect of the invention, the support portion and the terminal end form a circle.

BRIEF DESCRIPTION OF THE DRAWINGS

FIG. 1 is a side view of a preferred embodiment of the stylet of the present invention inside a catheter tube, with the tube shown partially and in cross-section;

FIG. 2 is an enlarged view of the stylet shown in FIG. 1;

FIG. 3 is a perspective view of the stylet shown in FIGS. 1–2; and

FIG. 4 is a cross-section of the stylet taken along the line 4—4 of FIG. 2.

DETAILED DESCRIPTION OF THE PREFERRED EMBODIMENTS

As shown in FIG. 1, a stylet 10 is disposed within a catheter tube 12 to form a assembly. The catheter tube 12 is disclosed in the copending application entitled Non-Occluding Catheter Bolus, Serial No. 08/077,019 filed on Jun. 15, 1993 in the name of David G. Quinn et al., the disclosure of which is hereby incorporated by reference. Reference is also made to the Continuation-in-part application Ser. No. 08/217,446, filed Mar. 24, 1994 entitled Non-Occluding Catheter Bolus and in the name of David G. Quinn. The disclosure of this application is also incorporated by reference.

The catheter tube 12 has an internal passage 13 that receives the stylet 10 during the intubation process. The stylet 10 provides the required support for the flexible catheter tube 12 necessary during the intubation process.

The stylet 10 is constructed from a single strand of wire. The diameter of the wire forming the stylet 10 may vary depending on the size of the catheter tube in use. For example, in an 8 FR tube (having an outside diameter of 0.138 inches) the wire has an outside diameter of 0.014 inches. The wire is preferably formed from stainless steel (302 grade, natural metal, spring tempered).

The stylet 10 includes a body portion 30 having a distal end 31 and a proximal end 32.

The stylet 10 has a coiled circular loop 14 located at the distal end 31. The diameter of the loop 14 may be adjusted depending on the requirements of a particular catheter tube. For example, a loop 14 diameter of 0.060 inches is preferred for use with an 8 FR tube.

As shown in FIGS. 2–3, the circular loop 14 has a top portion 16, a proximal portion 18, a bottom portion 20 and a distal portion 22. The coiled circular loop 14 is formed such that the top portion 16, the bottom portion 20 and the distal portion 22 include two adjacent segments of wire. More particularly, these portions of the loop 14 in the stylet 10 have a thickness substantially equal to 2X the diameter of the wire. As shown in FIG. 4, the proximal portion 18 does not have adjacent segments of wire and, accordingly, has a thickness equal to the diameter of the wire.

The circular loop 14 is connected to the body 30 of the stylet 10 by first and second legs 26 and 28. The legs 26 and 28 converge from the top and bottom portions 16 and 20 of the loop 14, respectively, where they are spread apart, to the distal end 31 of the stylet body 30, where they come together.

The loop 14 and support legs 26 and 28 form a tip on the stylet 10 which cannot readily deform. The proximal portion 18 of the loop forms a support between the top and bottom portions 16 and 20 of the loop and the spread apart legs 26 and 28 and, as such, prevents them from deforming, i.e., spreading further apart and enlarging the tip or terminal end of the stylet 10, for example. As such, the proximal portion 18 of the loop 14 is an important aspect of the present invention.

In this preferred embodiment, the body portion 30 of the stylet 10 is formed from first and second wire segments 33 and 34, as illustrated. They are twisted together to form a double helix. As previously pointed out, the loop 14 in this embodiment includes portions 16, 20 and 22 which are also formed from just two wire segments, while the loop portion 18 and the legs 26 and 28 are formed from single segments.

It should be understood, however, that the loop 14 may be formed such that the portions 16, 20 and 22 comprise more than two wire segments (three or more). In turn, the loop portion 18 forming the support may be formed with more than one wire segment (two or more).

In order to construct the stylet 10, a single strand of wire is bent in half and, at the bend is wrapped one or more times around a circular post. Accordingly, the circular loop 14 is created. The free ends of the two halves of the single strand of wire are the secured and the circular post is rotated in order to form the body portion 30. The rotation of the post causes the two halves of the single strand of wire to wrap around each other such that the body portion 30 forms a double helix type configuration.

While the invention has been described with reference to preferred embodiment, it should be understood that various changes may be made and equivalents may be substituted for elements thereof without departing from the scope of the invention. The scope of the invention is defined by the appended claims, and all devices that come within the meaning of the claims, either literally or by equivalents, are intended to be embraced therein.

I claim:

1. A catheter tube assembly, comprising:
    a) a catheter tube having a passage therein and a stylet disposed in said passage;
    b) said stylet including an elongate body portion and an insertion end;
    c) said insertion end including a loop and a pair of connecting legs separate from said loop and connecting said loop to said body portion;
    d) said loop including a terminal portion, opposed top and bottom portions and a proximal portion opposite said terminal portion;
    e) said connecting legs extending between said top and bottom portions of said loop and said elongate body portion, and converging toward said body portion;
    f) said terminal portion and said top and bottom portions of said loop forming a terminal end on said stylet;
    g) said proximal portion of said loop comprising a support portion for said insertion end of said stylet which is effective to prevent deformation of said loop and said connecting legs, said proximal portion being separate from said connecting legs.

2. The catheter tube assembly of claim 1 wherein said terminal end and said support portion form a circular loop.

3. The catheter tube assembly of claim 2 wherein said connecting legs leg form a V-shape.

4. The catheter tube assembly of claim 2 wherein said stylet is made from wire.

5. A stylet for use in the intubation of a catheter tube, comprising:
    a) an elongate body portion having a distal end and a proximal end;
    b) a loop having a top portion, a proximal portion, a bottom portion and a distal portion;
    c) said loop being connected to said body portion by first and second legs extending between said top and bottom portions of said loop, respectively, and said distal end of said body portion;
    d) said proximal portion of said loop comprising a support portion extending between said legs, said proximal portion being separate from said legs;
    e) said top, distal and bottom portions of said loop forming a terminal end on said stylet.

6. The stylet of claim 5 wherein said terminal end and said support portion form a circular loop.

7. The stylet of claim 6 formed from a single piece of wire.

8. The stylet of claim 7 wherein said body portion comprises a first segment and a second segment wrapped around each other in a double helix formation.

9. The stylet of claim 6 wherein said first leg and said second leg form a V-shape.

10. The stylet of claim 7 wherein said wire is made from stainless steel.

11. A catheter tube assembly, comprising:
    a) a catheter tube having a passage therein and a styler disposed in said passage;
    b) said stylet being fabricated of wire and including an elongate body portion having a distal end and a proximal end;
    c) a substantially circular loop connected to the distal end of said body portion and having a diameter slightly less than the diameter of said catheter tube passage, said loop defining a plane and said body portion adjacent said loop being substantially coplanar therewith;
    d) said substantially circular loop comprising a top portion, a proximal portion, a bottom portion and a distal portion, each of said top, distal and bottom portions of said loop comprising at least two adjacent segments of wire, said proximal portion of said loop comprising one less segment of wire than said top, distal and bottom portions;

e) said body portion comprising a first wire segment and a second wire segment wrapped around each other to form a double helix configuration.

12. The stylet of claim 11 wherein said wire is made from stainless steel.

13. A catheter tube assembly, comprising:

a) a catheter tube having a passage therein and a stylet disposed in said passage;

b) said stylet including an elongate body portion having a distal end and a proximal end;

c) said stylet also including a loop having a top portion, a proximal portion, a bottom portion and a distal portion with each of said top, distal and bottom portions comprising at least two adjacent wire segments and said proximal portion comprising one less segment of wire than said top, distal and bottom portions, said loop defining a plane and said body portion adjacent said loop being substantially coplanar therewith.

14. The stylet catheter tube assembly of claim 13 wherein said proximal portion comprises only a single segment of said wire.

15. A stylet for use in the intubation of a catheter tube, comprising:

a) a stylet including an elongate body portion having a distal end and a proximal end;

c) said stylet also including a loop having a top portion, a proximal portion, a bottom portion and a distal portion with each of said top, distal and bottom portions comprising at least two adjacent wire segments and said proximal portion comprising one less segment of wire than said top, distal and bottom portions, said loop defining a plane and said body portion adjacent said loop being substantially coplanar therewith.

\* \* \* \* \*